(12) United States Patent
Jung et al.

(10) Patent No.: US 8,821,232 B2
(45) Date of Patent: Sep. 2, 2014

(54) PLATFORM APPARATUS FOR SERIOUS GAME

(75) Inventors: Jae Bum Jung, Seoul (KR); Moon Gee Choi, Seoul (KR); Hyeon Woo Yi, Seoul (KR)

(73) Assignee: Jae Bum Jung, Songpa-Gu Seoul (KR)

( * ) Notice: Subject to any disclaimer, the term of this patent is extended or adjusted under 35 U.S.C. 154(b) by 0 days.

(21) Appl. No.: 13/414,507

(22) Filed: Mar. 7, 2012

(65) Prior Publication Data

US 2013/0288758 A1 Oct. 31, 2013

(30) Foreign Application Priority Data

Feb. 20, 2012 (KR) .......................... 10-2012-0016939

(51) Int. Cl.
*A63F 13/10* (2006.01)
*A63F 13/00* (2014.01)

(52) U.S. Cl.
CPC ............... *A63F 13/005* (2013.01); *A63F 13/10* (2013.01)
USPC ............................................................. 463/7

(58) Field of Classification Search
CPC .................. A63F 13/005; A63F 13/10; A63F 2300/8064; A63F 2300/807
USPC ........... 463/16, 20, 11–13, 17–19, 25, 26–28, 463/30–32, 40–42, 7, 9, 29, 36; 434/236–238, 322, 335, 336, 350, 351, 434/362; 600/544, 300; 128/920
See application file for complete search history.

(56) References Cited

U.S. PATENT DOCUMENTS

| | | | | |
|---|---|---|---|---|
| 5,911,581 A * | 6/1999 | Reynolds et al. | ............. | 434/236 |
| 6,435,878 B1 * | 8/2002 | Reynolds et al. | ............. | 434/236 |
| 8,382,484 B2 * | 2/2013 | Wetmore et al. | ............. | 434/236 |
| 2012/0308972 A1 * | 12/2012 | Miller et al. | .................. | 434/236 |
| 2013/0046206 A1 * | 2/2013 | Preminger | .................... | 600/595 |
| 2014/0057232 A1 * | 2/2014 | Wetmore et al. | ............. | 434/236 |

FOREIGN PATENT DOCUMENTS

| | | |
|---|---|---|
| KR | 1020040009045 A | 1/2004 |
| KR | 1020090039012 A | 4/2009 |
| KR | 1020110125059 A | 11/2011 |

* cited by examiner

*Primary Examiner* — David L Lewis
*Assistant Examiner* — Matthew D Hoel
(74) *Attorney, Agent, or Firm* — Kenneth E. Horton; Kirton McConkie

(57) ABSTRACT

A platform apparatus that processes the execution results of one or more serious games, the platform apparatus comprising a data processing unit that receives output packets produced from each serious game in execution for measuring and developing a user's cognitive abilities and that generates game data from the output packets; an analysis processing unit that generates, based on the game data, analysis data for measuring the user's brain function; and a result display unit that displays the analysis data to the user through an UI (user interface), wherein the one or more serious game includes serious games for memory, for psycho-motor, for attention, for executive function, and for emotion.

8 Claims, 18 Drawing Sheets

FIG. 2

| SERIOUS GAME OUTPUT PACKET | | | |
|---|---|---|---|
| Index | DATA | DATA TYPE | EXPLANATION |
| 1 | id | int | ID OF CHARACTER, MADE UP OF NUMBERS |
| 2 | name | varchar | NICKNAME OF CHARACTER |
| 3 | sex | boolean | SEX OF CHARACTER |
| 4 | level | int | LEVEL OF CHARACTER |
| 5 | current_exp | int | CURRENT EXPERIENCE VALUE OF CHARACTER |
| 6 | map_ID | int | MAP ID |
| 7 | status_str | int | STRENGTH OF CHARACTER |
| 8 | status_int | int | INTELLECTUAL POWER OF CHARACTER |
| 9 | status_dex | int | AGILITY OF CHARACTER |
| 10 | current_hp | int | CURRENT HP OF CHARACTER |
| 11 | max_hp | int | MAXIMUM HP OF CHARACTER |
| 12 | current_mp | int | CURRENT HP OF CHARACTER |
| 13 | min_mp | int | MINIMUM HP OF CHARACTER |
| 14 | char_3D_xy | int | WORLD COORDINATES OF CHARACTER |
| 15 | char_xy | int | PROJECTION COORDINATES OF CHARACTER |
| 16 | current_tool | int | CURRENT TOOL OF CHARACTER |
| 17 | current_cmagic | int | CURRENT MAGIC OF CHARACTER |
| 18 | mouse_time | int | MOUSE CLICK TIME |
| 19 | mouse_x | int | X COORDINATE OF MOUSE POINTER |
| 20 | mouse_y | int | Y COORDINATE OF MOUSE POINTER |
| 21 | coll_flag | int | COLLISION CHECK FLAG |
| 22 | coll_obt | int | ID OF COLLISION OBJECT |
| 23 | response_sec | int | CHARACTER RESPONSE (SEC) |
| 24 | item_power | int | POWER OF ITEM |
| 25 | correct_rate | float | CORRECT ANSWER RATE WITH RESPECT TO STIMULUS |
| 26 | error_rate | float | ERROR RATE WITH RESPECT TO STIMULUS |

FIG. 4
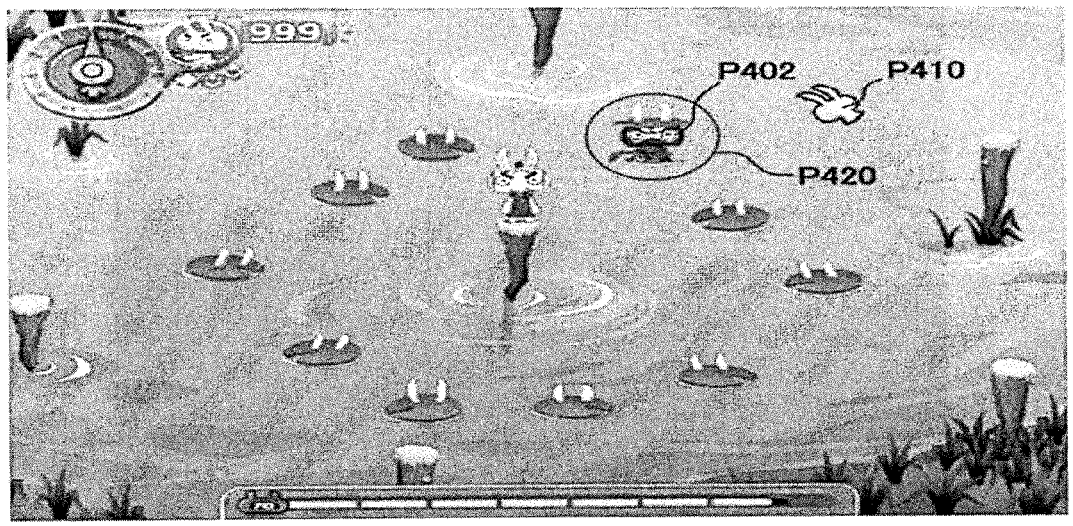
(a)
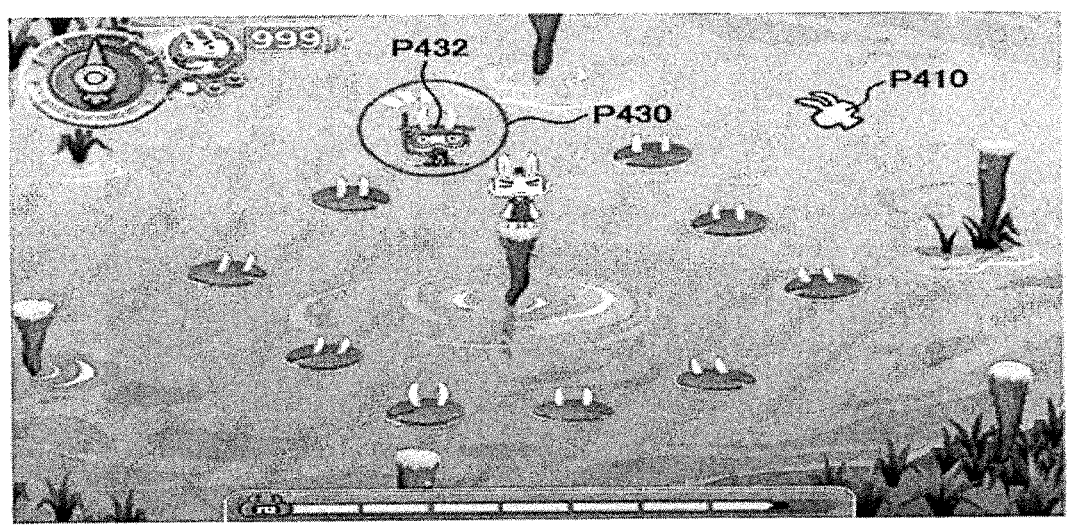
(b)

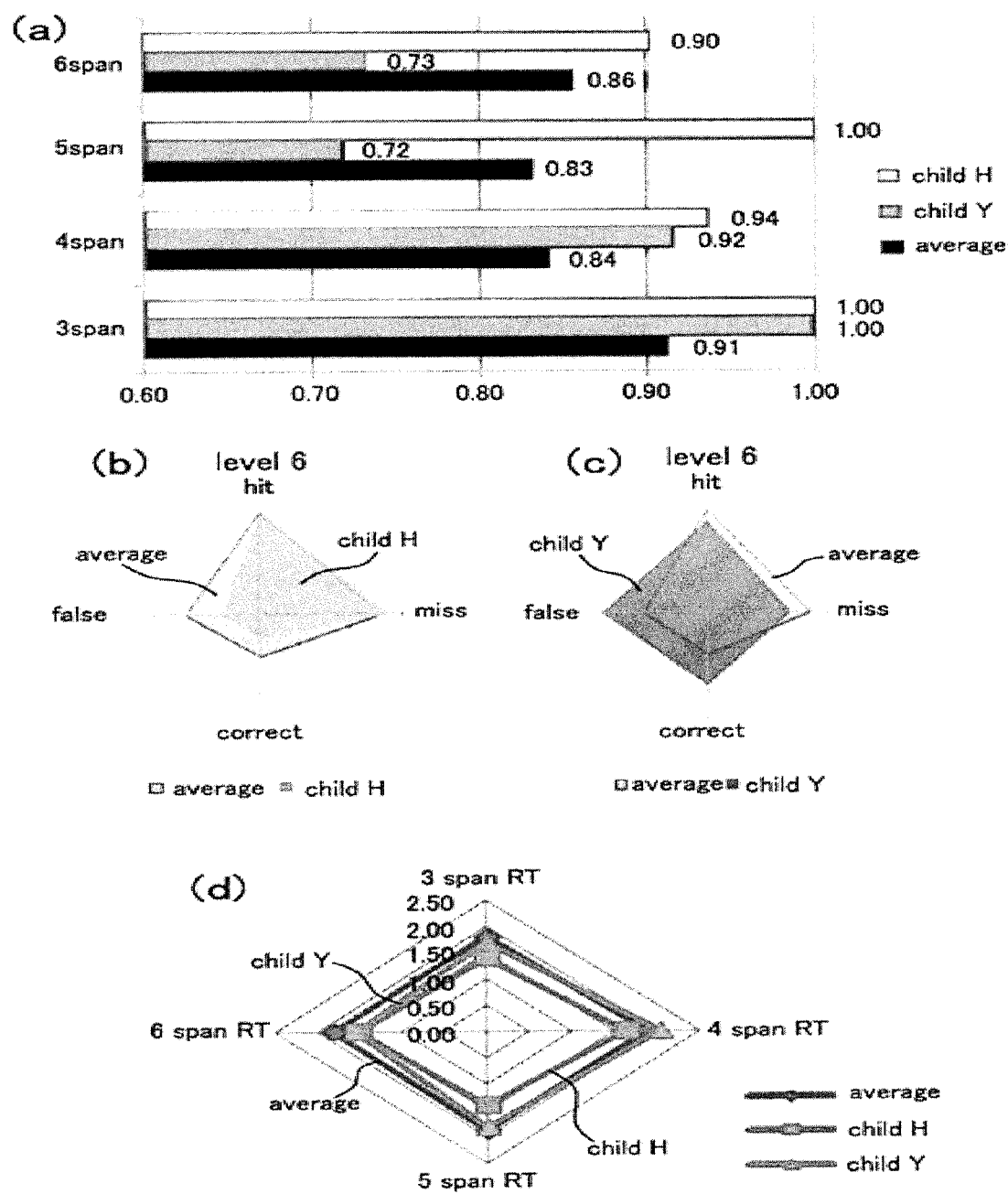

FIG. 8B
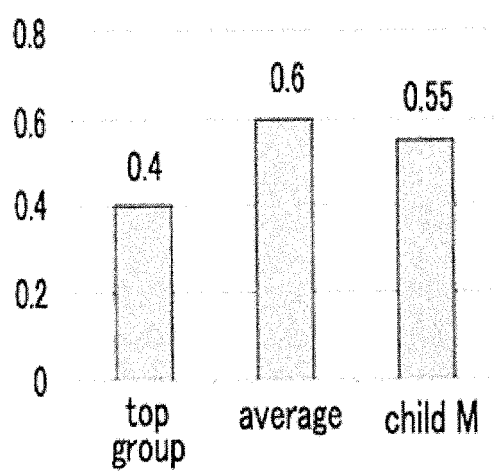
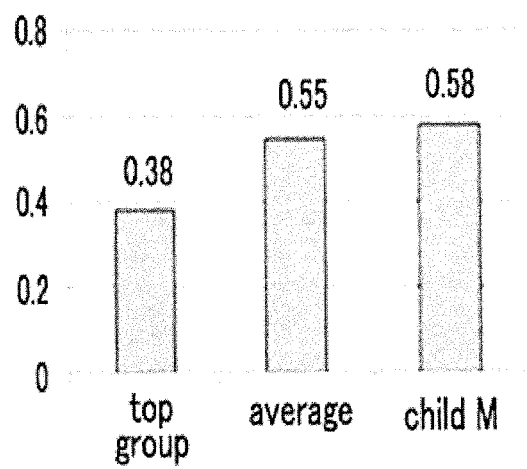
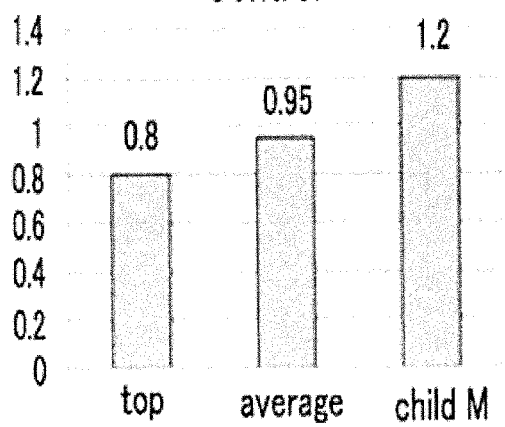
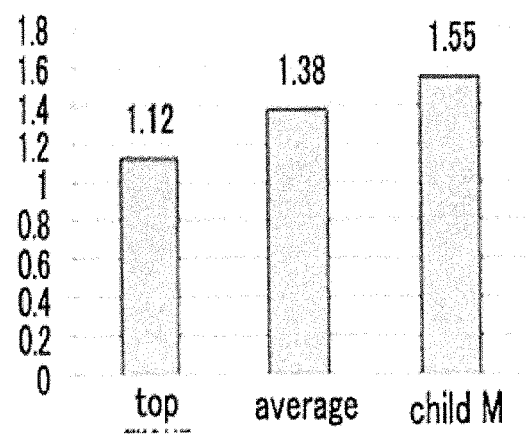

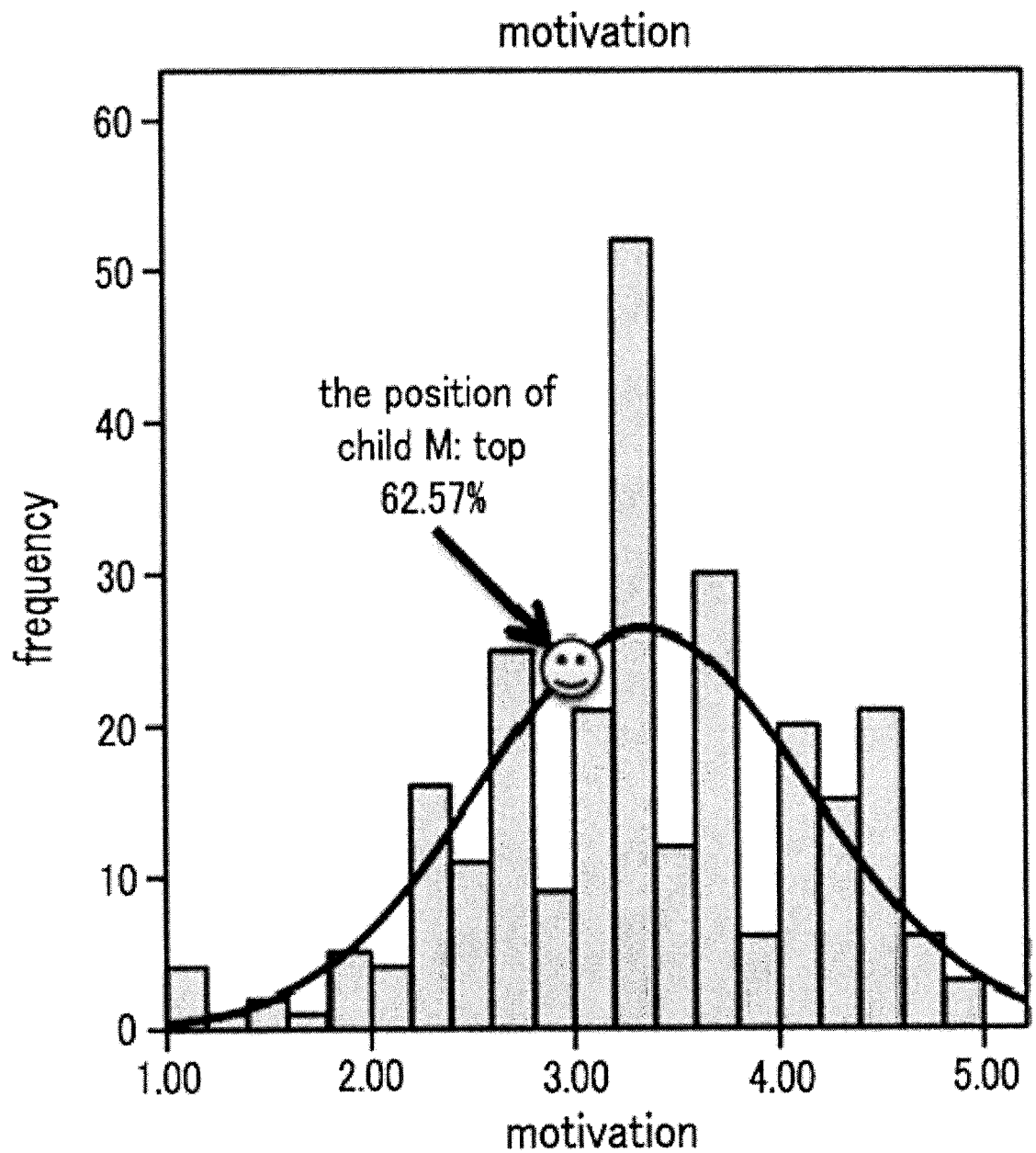

*FIG. 10*
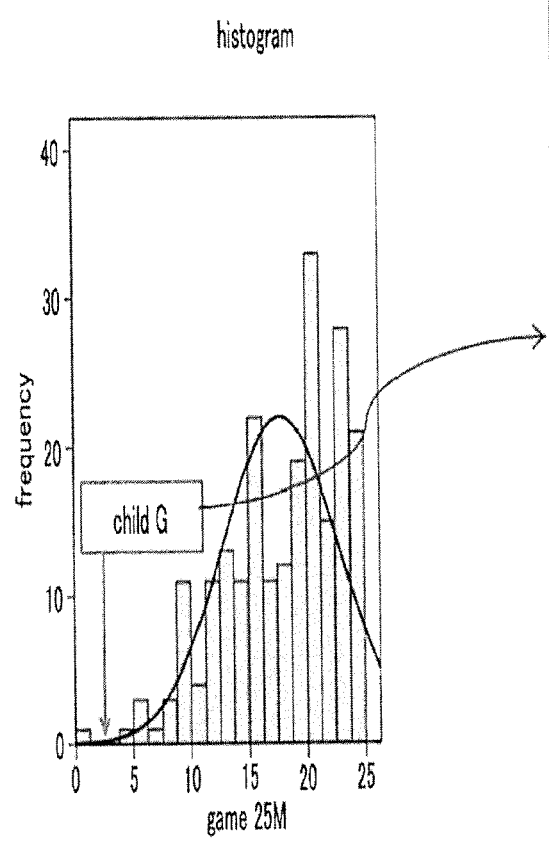
(a)
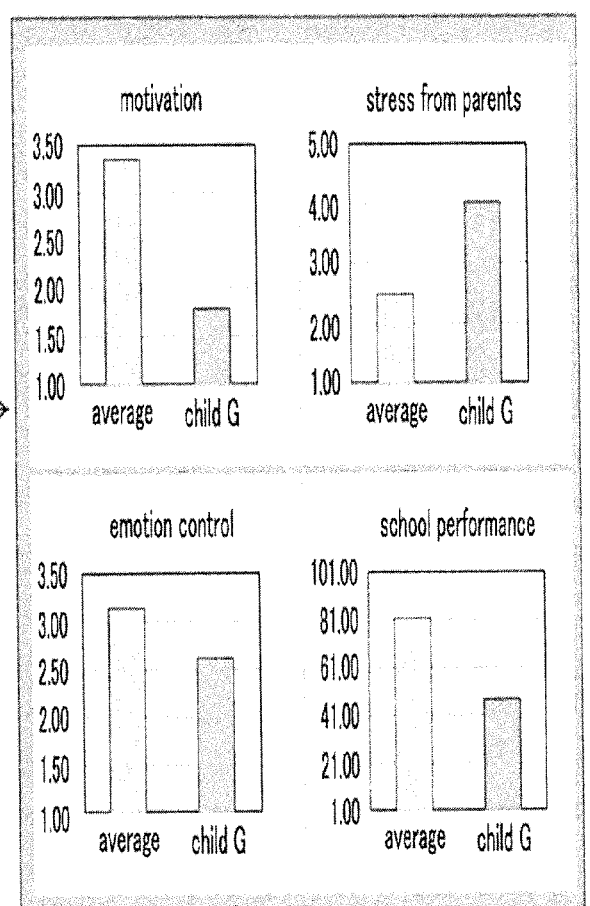
(b)

*FIG. 11B*

General:
Your main cognitive functions are excellent. Your intelligence is in general based on logical thinking and fast understanding of situations. You are sensitive to environmental changes and can adapt fast and effectively to them. However, this ability is limited to knowledge-based situation. Because your emotional intelligence is relative low, you need more social skills and abilities to understand others.

| Cognition | TQ | Position | Performance |
|---|---|---|---|
| Memory D | 107 | Top 15% | High |
| Attention B | 116 | Top 7% | Very high |
| Executive Function A | 114 | Top 9% | High |
| Psycho-Motor E | 100 | Top 50% | Low |
| Emotion F | 88 | Top 69% | Very Low |

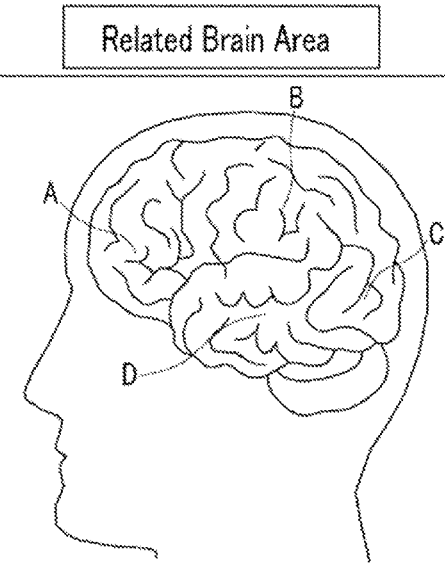

Related Brain Area

PLATFORM APPARATUS FOR SERIOUS GAME

CROSS-REFERENCE TO RELATED APPLICATION

This application claims the benefit of Korean Patent Application No. 10-2012-0016939 filed on Feb. 20, 2012, the entire disclosures of which are incorporated herein by reference.

FIELD OF THE INVENTION

The present disclosure relates to a platform apparatus that processes the execution results of serious games for measuring and developing cognitive abilities.

BACKGROUND OF THE INVENTION

As an online game is continuously popular, a game industry has rapidly grown. Further, serious games applicable to education, training, medical treatment, and exercise have attracted great attention.

The serious games are structured activities designed by combining an original purpose of entertaining humans to have happiness and fun and a proper functional purpose of helping humans in doing disagreeable activities without aversion. In early days, the serious games were designed for military purpose. In recent years, the serious games have been developed and used in various genres and in various fields, such as education, training, medical treatment and public services.

Meanwhile, a cognitive ability is a primary faculty for mental activities and may be involved in all processes of rapidly and efficiently processing and analyzing information from the surrounding environment. That is, the terms "cognition" refers to active metal processes including awareness, attention, remembering, learning, producing and understanding language, thinking, feeling, solving problems, and doing skilled activities.

If there is a lack of a cognitive ability, a child may have developmental disabilities or developmental delays and also may have a speech defect, an attention disorder, and poorness of processing information, which may cause him/her difficulty in leading a social life.

Therefore, a cognitive ability testing service for checking a decline or delay in a cognitive ability and a service helpful for developing a cognitive ability through a training of repeated use of the cognitive ability to prevent a decline or delay in the cognitive ability have attracted great attention.

As a conventional cognitive ability test, there are Korean-Wechsler Intelligence Scale, Kaufman Assessment Battery for Children (K-ABC), KWIS, and Ray-Kim Test as one of Korean memory test.

To be specific, Korean-Wechsler Intelligence Scale is used to measure an intelligent quotient (IQ) through subtests including a verbal test and a performance test, and K-ABC is used to measure an IQ and achievement through a mental processing test and an achievement test and places more emphasis on mental processing. KWIS is made up of a verbal scale and a performance scale including various subtests such as general information, picture completion, arithmetic, and the like and used to generally assess a personal ability. Ray-Kim Test places more emphasis on memory and is made up of an auditory verbal learning test and a complex figure test to measure a degree of memory retention, an efficiency of retrieval, and the like.

Such conventional cognitive ability tests have been used to measure a cognitive ability as defined in each test. However, they focus on only a part of cognitive ability such as an IQ or memory. Therefore, a cognitive ability test capable of generally measuring a cognitive ability having various functions as well as a memory function is needed.

Generally, conventional cognitive ability measurement and development services have been served offline. That is, a user who wants to get a cognitive ability measurement and development service is required to visit a specialize agency such as a hospital and based on an expert's analysis on the user's answers in written form or questions and answers during an interview, the user can check his/her own cognitive ability or can get a training for developing his/her own cognitive ability.

Therefore, the conventional cognitive ability measurement and development services have low accessibility due to insufficient special agencies, a long time required to provide a service, high cost and a user's inconvenience caused by a personal visit. Further, a cognitive ability measurement entirely depends on experience and knowledge of an expert and statistical data based thereon, and, thus, reliability of the service cannot be improved. Furthermore, the questions and answers for the conventional cognitive ability measurement and development are made up of boring contents, and, thus, the user may lose interest easily.

In order to measure and develop cognitive abilities by means of serious games, various types of serious games need to be developed. In order to do so, a serious game development environment in which various developers can develop various serious games freely to make profits needs to be promoted. Therefore, while various serious games are developed in different ways, a common platform capable of executing such various serious games in a integrated way is needed.

In this regard, Korean Patent Laid-open Publication No. 2009-0010874 (entitled "System and method for developing cognitive function based on web service and recording medium using by the same") discloses a system for measuring and developing cognitive abilities by means of a web service.

BRIEF SUMMARY OF THE INVENTION

Illustrative embodiments of the present disclosure provide a serious game execution output processing platform apparatus which is capable of processing the execution results of various serious games for measuring and developing cognitive abilities and of displaying the analysis results thereof.

In view of the foregoing, there is provided a platform apparatus that processes the execution results of one or more serious games, the platform apparatus comprising a data processing unit that receives output packets produced from each serious game in execution for measuring and developing a user's cognitive abilities and that generates game data from the output packets; an analysis processing unit that generates, based on the game data, analysis data for measuring the user's brain function; and a result display unit that displays the analysis data to the user through an UI (user interface), wherein the one or more serious game includes one or more of a serious game for memory, a serious game for psycho-motor, a serious game for attention, a serious game for executive function, and a serious game for emotion, the output packets contain one or more of information of a user playing the serious game, information of a character used by the user during execution of the serious game, time information of the user for operating the input device, position information of a cursor the user controlling via the input device, information of a collision between the character and objects appearing in the serious game, a correct answer rate of the user's response to events in the game, and a reaction error rate of the user's response to the events, and the game data contains one or more of a reaction time of the user to the events occurring during the execution of the serious game, a reaction error rate of the user's response to the events, and an accumulated distance of the cursor movement during the execution of the serious game.

The present invention provides a platform apparatus capable of processing the output data from various serious games for measuring and developing a user's cognitive abilities. Therefore, game developers can more easily develop serious games applicable to the platform apparatus, while game users can enjoy a wider variety of serious games.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which:

FIG. 2 illustrates the raw data information contained in an output packet produced from the serious game in execution in accordance with the present invention;

FIGS. 3 to 6 show exemplary embodiments of serious games applicable to the platform apparatus in accordance with the present invention; and FIGS. 7 to 11 are provided to illustrate the exemplary contents of the analysis data in accordance with the present invention.

DETAILED DESCRIPTION OF THE INVENTION

Figure 1:
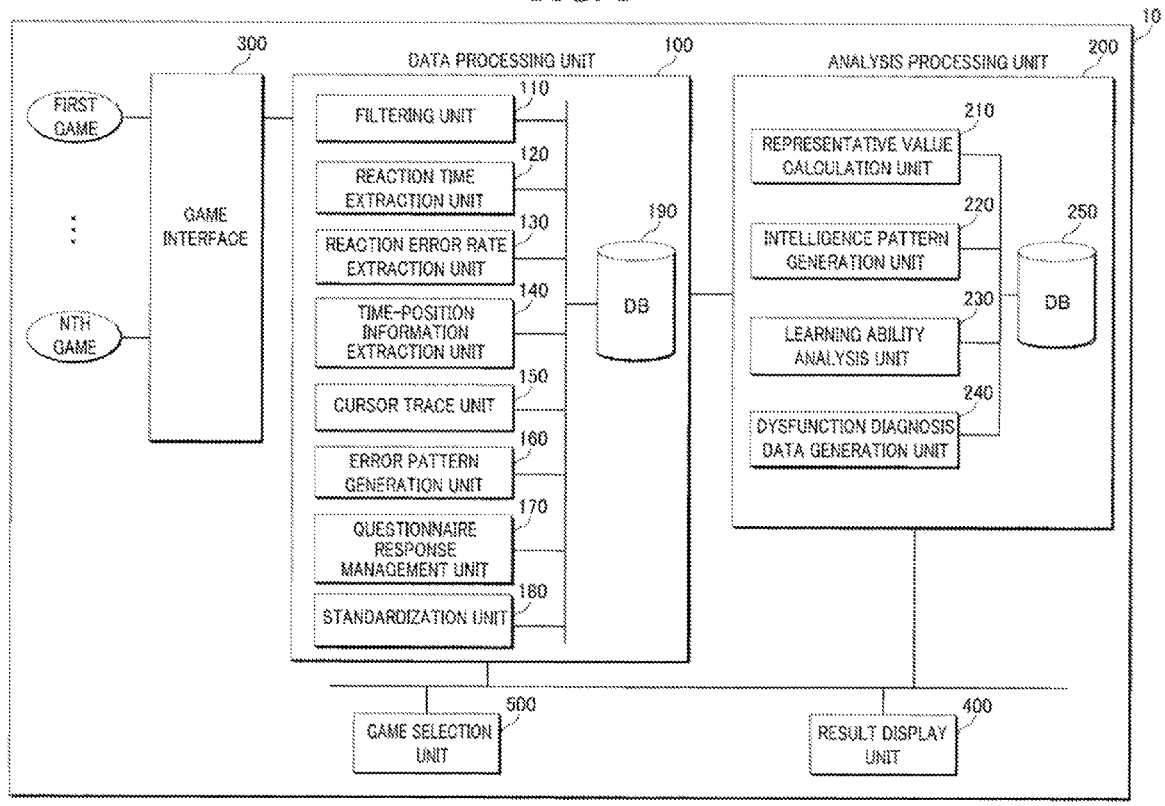
FIG. 1 illustrates a platform apparatus that processes the execution results of one or more serious games in accordance with the present invention.
Figure 3:

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the terms "connected to" or "coupled to" that is used to designate a connection or coupling of one element to another element includes both a case that an element is "directly connected or coupled to" another element and a case that an element is "electronically connected or coupled to" another element via still another element. Furthermore, the terms "comprises or includes" and/or "comprising or including" used in the document means that one or more other components, steps, operation and/or existence or addition of elements are not excluded in addition to the described components, steps, operation and/or elements unless context dictates otherwise.

FIG. 1 illustrates a platform apparatus that processes the execution results of one or more serious games in accordance with the present invention.

A platform apparatus 10 includes a data processing unit 100, an analysis processing unit 200, a game interface 300, a result display unit 400, and a game selection unit 500. Components illustrated in FIG. 1 in accordance with the illustrative embodiment are software or hardware components such as a FPGA (Field Programmable Gate Array) or an ASIC (Application Specific Integrated Circuit) to perform certain operations.

However, the components are not limited to the software or the hardware, and each of the components may be stored in an addressable storage medium or may be configured to implement one or more processors.

Accordingly, the components may include, for example, software, object-oriented software, classes, tasks, processes, functions, attributes, procedures, sub-routines, segments of program codes, drivers, firmware, micro codes, circuits, data, database, data structures, tables, arrays, variables and the like.

The components and functions thereof can be combined with each other or can be divided.

The platform apparatus 10 can process various types of serious games for measuring and developing a user's cognitive abilities. By way of example, serious games for memory, serious games for psycho-motor, serious games for attention, serious games for executive function, and serious games for emotion can be processed by the platform apparatus 10. Furthermore, the serious games for memory can be subcategorized into serious games for word short-term memory, digit short-term memory, spatial memory, music memory, and shape memory. The serious games for psycho-motor can be subcategorized into serious games for motor programming, motor-cognition coordination, and motor control. The serious games for attention can be subcategorized into serious games for selective attention, attention shift, spatial attention, divided attention, and automatization. The serious games for executive function can be subcategorized into serious games for working memory, rule shift, cognitive control, categorization, and logical thinking. The serious games for emotion can be subcategorized into serious games for emotional perception, emotion control, emotional memory, motivation, and emotional state.

FIGS. 3 to 6 show exemplary embodiments of serious games applicable to the platform apparatus in accordance with the present invention. For example, the serious game depicted in FIG. 3 can be used for measuring or developing the user's memory. The game first presents several words to the user to memorize. Then it displays a plurality of words for a limited time. If the user selects a previously presented word from the plurality of words, it is regarded as a correct answer. The difficulty level of the game can be adjusted with factors like the type or of the presented words and the number thereof. That is, when the word objects P330 and P320 appear in the game, the user moves the aiming point P310 to select one of the word objects P330 and P320, and if the selected word object is determined to be one of the previously presented words, the game regards it as a correct answer. Also, with further consideration for the reaction time of the user to the appearance of the word objects, the user's memory can be analyzed. The user's ability to memorize or attend to words can be measured and developed by means of such a game.

The serious game depicted in FIG. 4 can also be used for measuring or developing the user's memory. The game presents objects P402 and P432, some of them different from the others, at predetermined positions P420 and P430 for a certain time period for the user to memorize. Then, for a limited time, the user should select an object with an aiming point P410. Whether or not the answer is correct depends on whether or not the user selects the objects previously presented as different from the others in the game. Also, with further consideration for the reaction time of the user to the appearance of the word objects, the user's memory can be analyzed. The user's ability to memorize and attend to the position of objects can be measured and developed by means of such a game.

Figure 5:
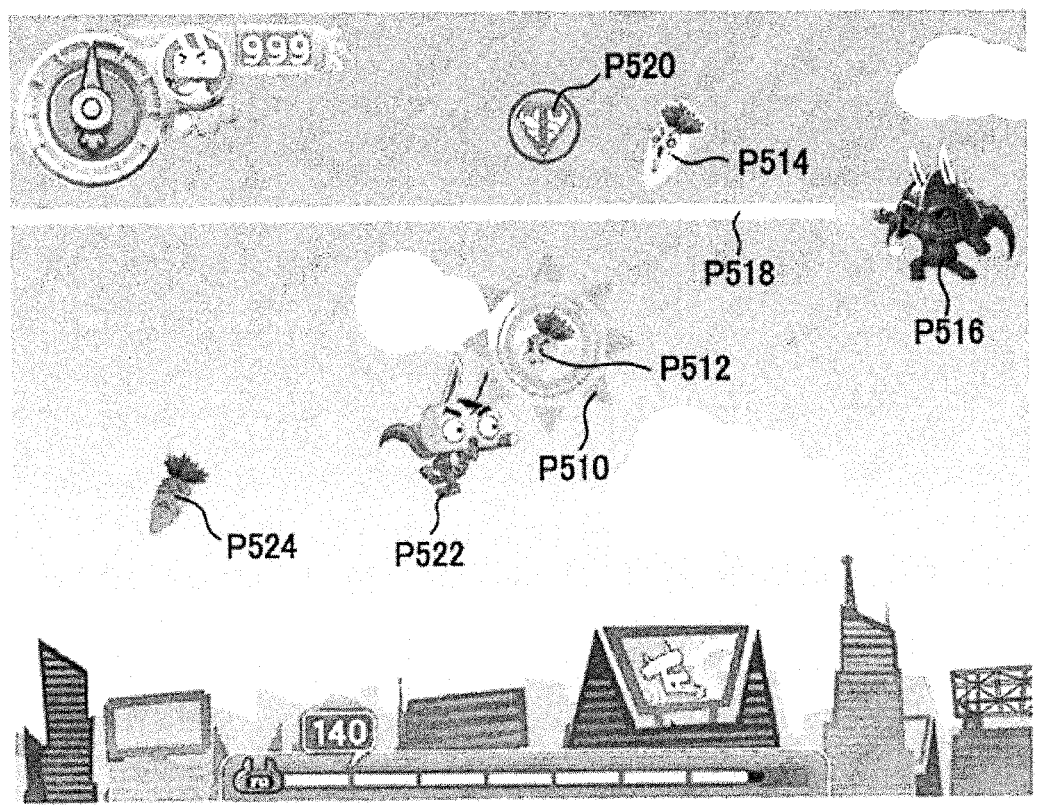

The serious game depicted in FIG. 5 can be used for measuring or developing the user's psycho-motor and attention. In this serious game, the character P522 moves in the horizontal direction while trying to select only desirable objects from a plurality of objects P512, P514 and P524 with an aiming point P510. The feature of an object is indicated by means of, for example, its color. By way of example, an object in purple decelerates the character P522 and an object in orange color let the character P522 to score. There may be enemy characters P516 that try to block the character P522, so the character P522 should select the beneficial objects while avoiding the attacks of the enemy characters P516. This game can improve the user's eye-hand coordination, a sort of psycho-motor, through the task of finely controlling and moving the mouse to send the character to a desired position. Furthermore, by selecting a specific object from a plurality of objects, the user can improve selective attention, a sort of attention.

Figure 6:
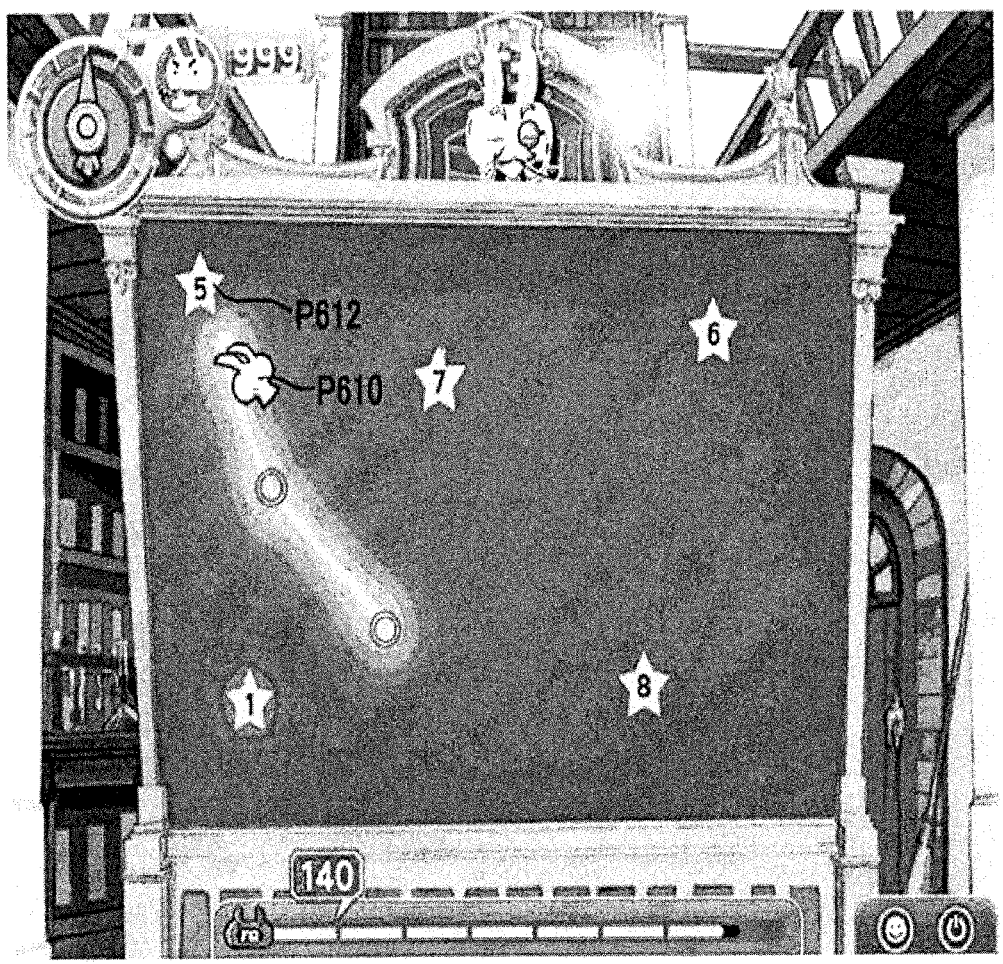

The serious game depicted in FIG. 6 can also be used for measuring or developing the user's attention. In this serious game, the objects (numbers or words etc.) are presented one by one in a predetermined order. Then, the user should use the mouse to move the aiming point to connect the objects appearing on the blackboard with one another. If the user connects the objects in the right order, scores will be given to the user. The difficulty level of the game can be adjusted with factors like the types or order of the objects appearing on the blackboard. The user's selective attention and attention shift, sorts of attention, can be measured and developed by means of such a game.

The above-described serious games are provided for illustration and it should be noted that more various types of serious games can be processed by a platform apparatus in accordance with the present invention.

Referring back to FIG. 1, the data processing unit 100 receives output packets produced from each serious game in execution and analyzes the received output packets to generate game data. The game data generated by the data processing unit 100 contains one or more information including the reaction time of the user to the events in the serious game, the reaction error rate of the user's response to the events, and the accumulated distance of the cursor movement during the execution of the serious game. The generated game data is stored in a database 190.

The data processing unit 100 includes a filtering unit 110, a reaction time extraction unit 120, a reaction error rate extraction unit 130, a time-position information extraction unit 140, a cursor trace unit 150, an error pattern generation unit 160, a questionnaire response management unit 170, and a standardization unit 180.

The filtering unit 110 filters an output packet produced from each serious game in execution to generate raw data.

FIG. 2 illustrates the raw data information contained in an output packet produced from the serious game in execution in accordance with the present invention.

As depicted in FIG. 2, the output packet may contain information including the user playing the serious game, the execution status of the serious game (ex: game identification information, game difficulty, and map ID), details of the character the user using during the execution of the serious game (ex: ID, nickname, sex, level, experience value), the times the user operating the input device (ex: a mouse clicking time or a keyboard typing time), the positions of the cursor the user controlling via the input device (ex: coordinates of the mouse pointer), the collisions between the character and the objects appearing in the serious game (ex: collision check flag and collision check ID), the correct answer rate of the user's response to the events in the game, and the reaction error rate of the user's response to the events.

As described above, the filtering unit 110 analyzes the output packet and classifies the various row data contained in the output packet.

Again, referring to FIG. 1, the reaction time extraction unit 120 extracts the reaction time of the user from the raw data. The reaction time of the user means the time taken for the user to operate the input device in response to an event or an object appearing in the serious game. By way of example, the reaction time can be calculated based on the difference between the event occurring time contained in the previous output packet and the input device operating time contained in the present output packet. Otherwise, the reaction time can be calculated based on the difference between the input device operating time contained in the last output packet and the input device operating time contained in the present output packet.

The reaction error rate extraction unit 130 extracts the reaction error rate of the user from the raw data. That is, during the execution of the serious game, when the user selects an object satisfying predetermined rules, it is regarded as a correct answer and if the user selects other objects, it is regarded as a wrong answer. Then, the reaction error rate is calculated based on the ratio of correct answers to wrong answers. It can be used as the error rate of the user's response to the input stimuli.

The time-position information extraction unit 140 extracts, from the raw data, the reaction time information of the user to two or more objects different objects appearing in the serious game and the difference of the positions where the input device was operated. From the extracted information, it is possible to obtain the time the user operated the input device at a first position and the time the user operated the input device at a second position. Based on the obtained information, the platform apparatus can determine whether the user manipulated the input device along the optimal route or it took a longer time for the user to manipulate the input device. That is, by comparing the obtained information to that of average users, the platform apparatus can determine whether or not it took the user a considerable time to manipulate the input device send the cursor to the second position from the first position, and, then, it can calculate cognitive abilities or motor function of the user.

A cursor trace unit 150 extracts, from the raw data, the accumulated distance of the cursor movement during the execution of the serious game. The accumulated distance, measured in pixel, can be used as a subsidiary factor to find out cognitive abilities or motor function of the user by calculating the efficiency of the user's reaction to the stimuli (for example, by comparing the movement distance to the shortest distance between the two points).

The error pattern generation unit 160 extracts the pattern of the correct and wrong answers of the user and stores the extracted pattern information into the database 190. By way of example, correct answers and errors of the user input with respect to various events occurring during the serious game are patterned and provided to the database 190.

The questionnaire response management unit 170 handles the answers of the user to a questionnaire for checking emotional state or cognitive abilities of the user. That is, the questionnaire is to be provided to the user before or after the execution of the serious game, and when the user submits the response data, the cognitive abilities of the user will be analyzed based on the response data. The questionnaire may contain structured questions related to the ego involvement of the user, such as opinions, decisions, attitudes, and emotions of the user.

The standardization unit 180 accumulates information contained in the data packets input through the game interface 300 for a certain time period to generate a normal distribution, and marks the input values out of a predetermined range in the normal distribution as errors. If the input value is in the predetermined range, it will be marked in advance as an error without having to be analyzed. By way of example, the input value may be processed before the data packet is transmitted to the filtering unit 110. But the input data may also be analyzed based on the data filtered by the filtering unit 110.

The analysis processing unit 200 generates analysis data for measuring the user's brain function based on various game data generated by the data processing unit 100. The analysis processing unit 200 includes a representative value calculation unit 210, an intelligence pattern generation unit 220, a learning ability analysis unit 230, and a dysfunction diagnosis data generation unit 240.

FIGS. 7 to 11 are provided to illustrate the exemplary contents of the analysis data in accordance with the present invention.

The representative value calculation unit 210 calculates a representative value, such as mean or median, for each cognitive ability domain, based on the reaction time of the user to an event, the reaction error rate, the accumulated distance of the cursor movement, and the like. The representative value for each cognitive ability domain can be displayed in various types of graphs as provided in FIG. 7. As depicted in FIG. 7(*a*), along with the average for the specific user, the total average of all users may be displayed in the graphs indicating the memory capability measured as scores for each digit number span in the digit span game. Also, as depicted in FIGS. 7(*b*) and 7(*c*), assessment results for correct answer rates and error rates may be displayed. Furthermore, as depicted in FIG. 7(*d*), average values of response times (RT) for each digit span may be displayed.

Figure 11A:
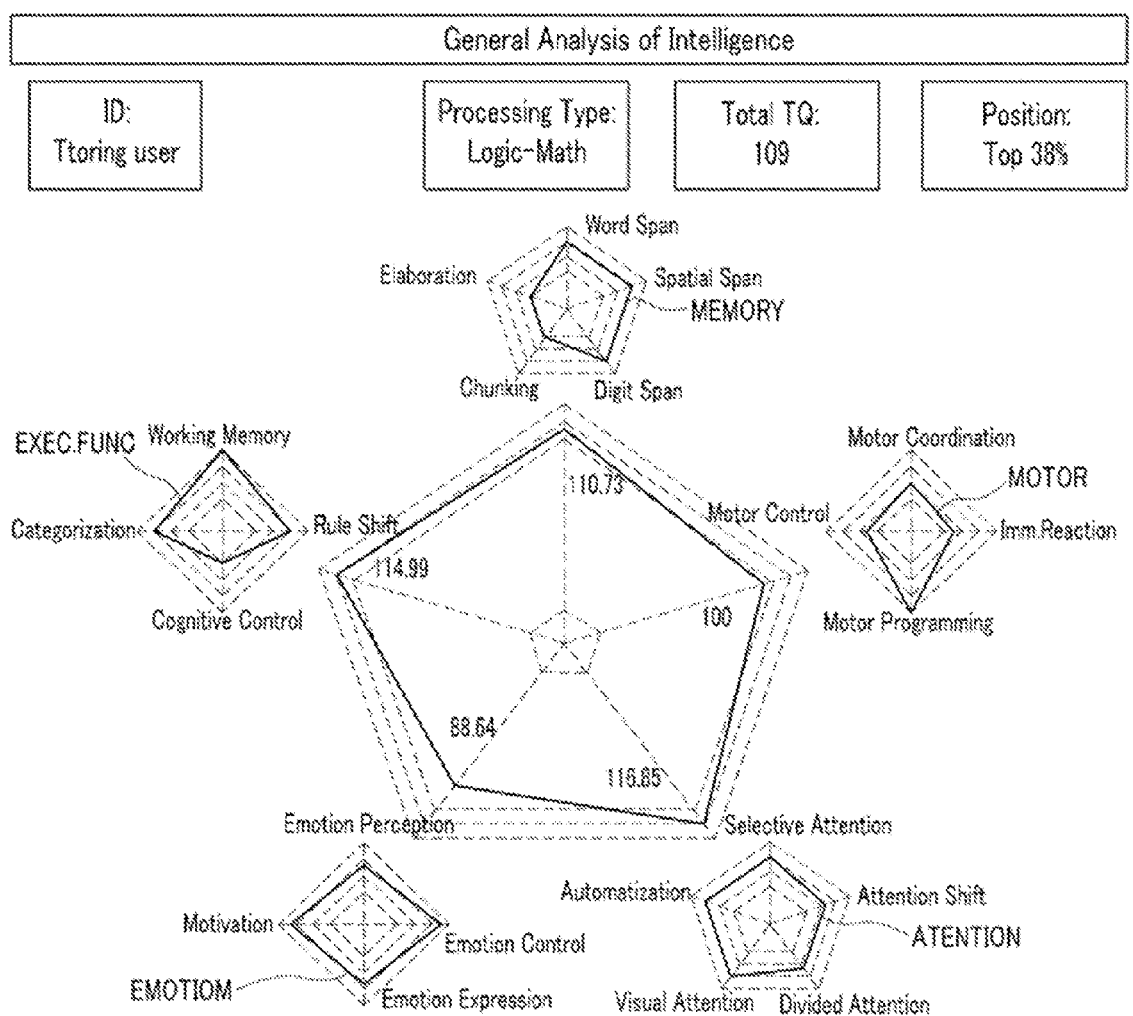

The intelligence pattern generation unit 220 generates the comprehensive intelligence pattern as well as intelligence pattern for each cognition and emotion domain, based on the game data of each section. The intelligence pattern graph indicating the comprehensive pattern of each individual's intelligent characteristics, as depicted in FIG. 11*a*, shows some of the comprehensive information including: in which area the individual has better abilities, in which area of abilities the individual has used and developed as his/her key ability, and in which area the individual is comparatively inferior to his/her other intelligences. The intelligence pattern is used to classify or diagnose the intelligent characteristics of the individual by obtaining the average IQ score and various categorized intelligence patterns of ordinary people and compare the individual's intelligence pattern results with them.

Figure 8A:
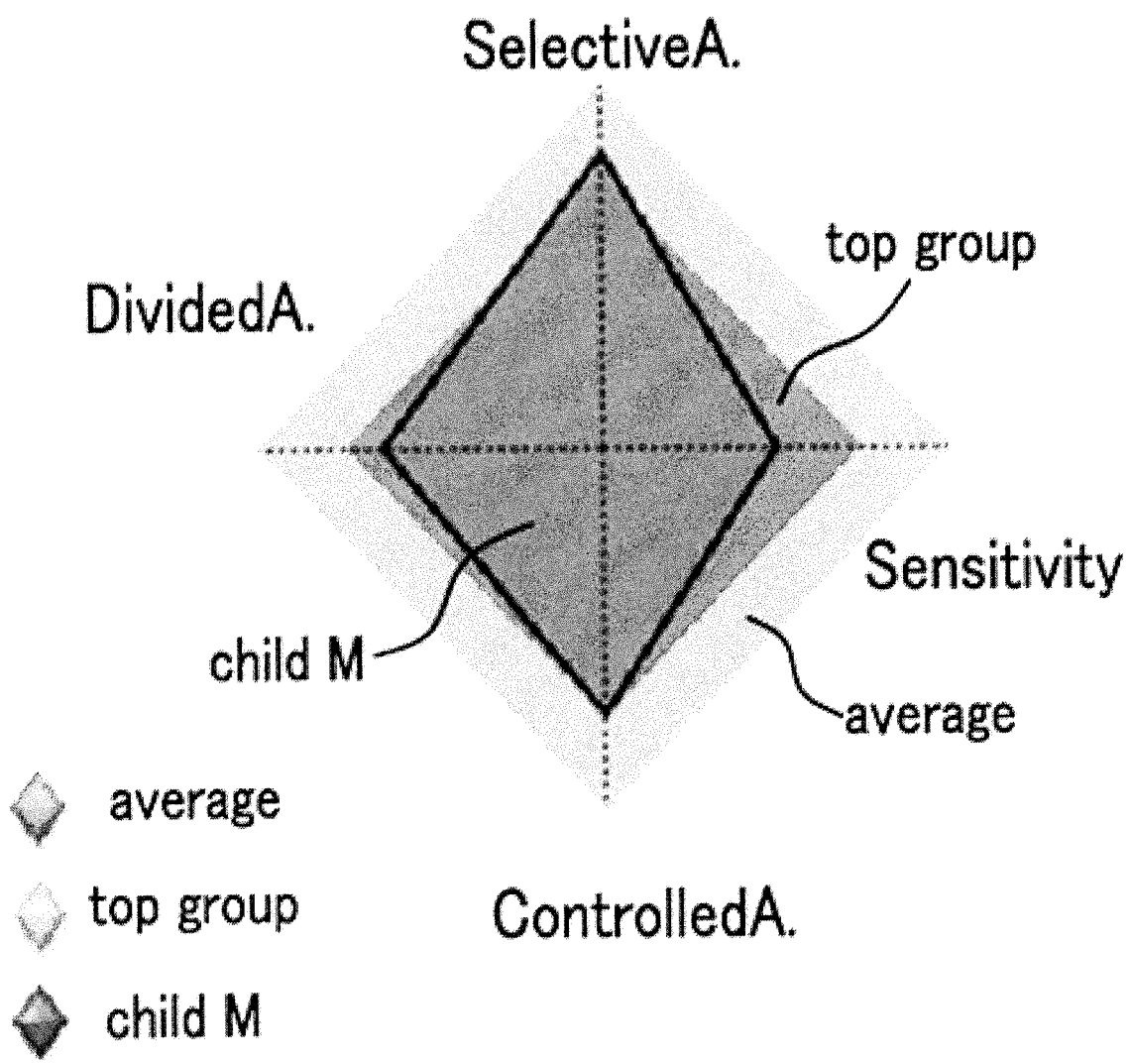
Figure 8C:
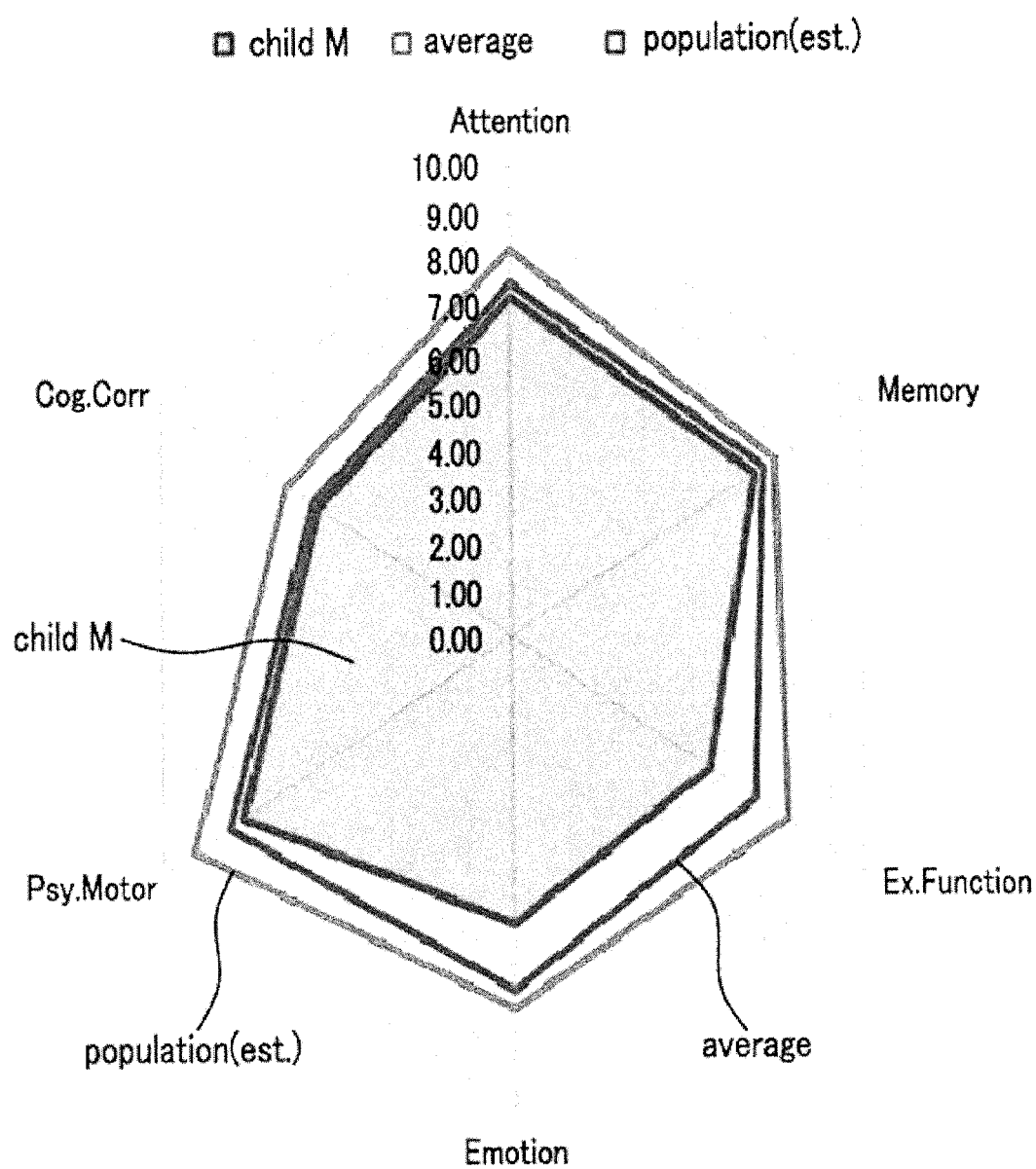

As depicted in FIG. 8, the intelligence pattern can be analyzed into more detailed areas and displayed in various types of graphs. By way of example, as depicted in FIG. 8(*a*), the intelligence patterns of selective attention (Selective A.), divided attention (Divided A.), sensitivity, and controlled attention (Controlled A.) can be displayed. Furthermore, as depicted in FIG. 8(*b*), the intelligence pattern of the user can be compared with a higher ranked group and the entire group for each subcategory. Furthermore, as depicted in FIG. 8(*c*), the intelligence pattern of the user can be displayed together with the intelligence patterns of the average users for all of the cognitive abilities.

The learning ability analysis unit 230 generates statistical learning ability comparison data based on the game data received from the data processing unit 100 the representative values for each cognitive ability domain received from the representative value calculation unit 210, and the intelligence pattern information received from the intelligence pattern generation unit 220. By way of example, the learning ability analysis unit 230 checks whether or not the user's school performance is consistent with the user's IQ score from a statistical view. That is, the learning ability analysis unit 230 checks whether there is a great gap between the school performance of a user whose evaluated IQ score is 100 and the demographically expected school performance of a person whose IQ score is 100.

Figure 9B:
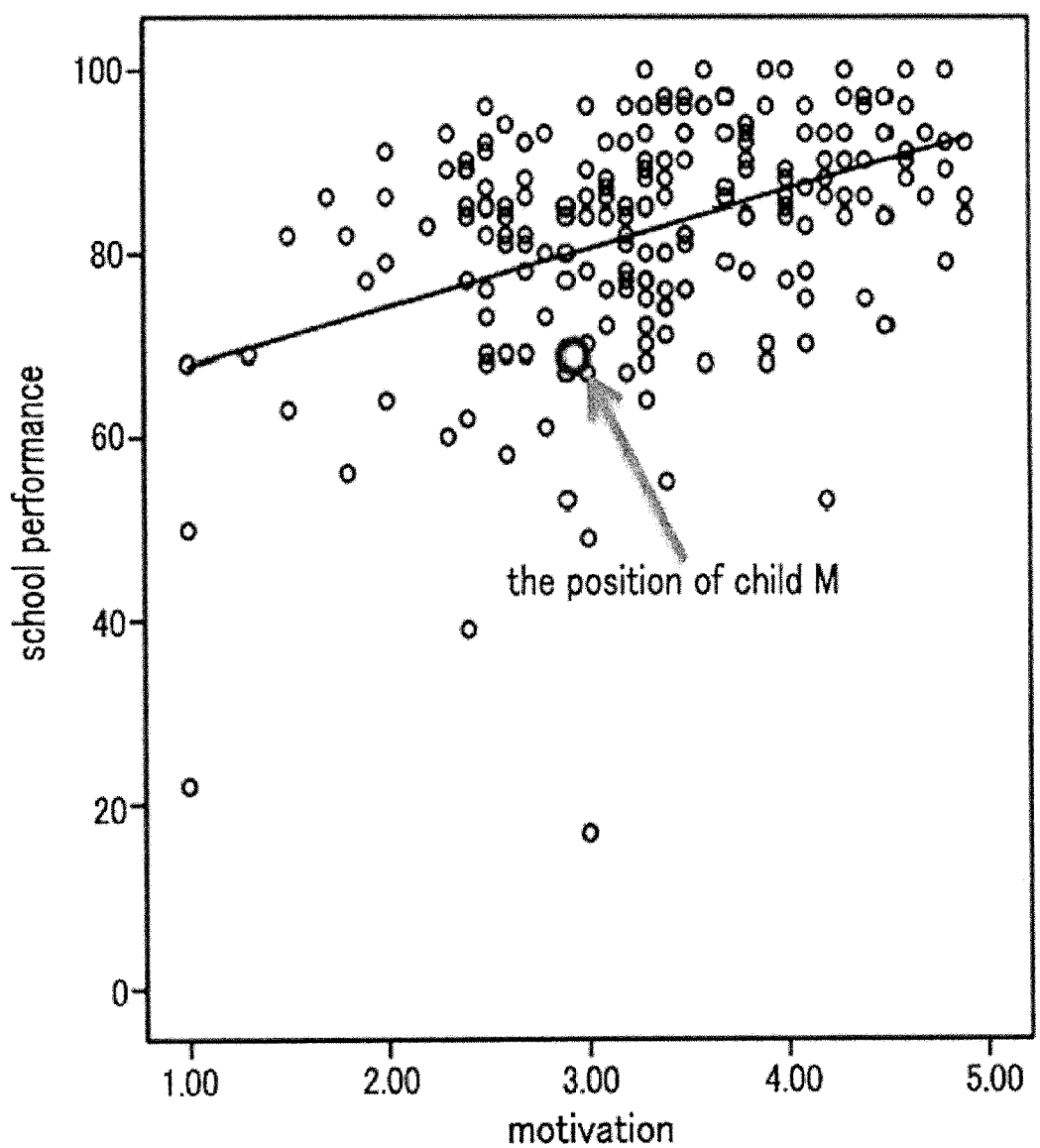
Figure 9C:
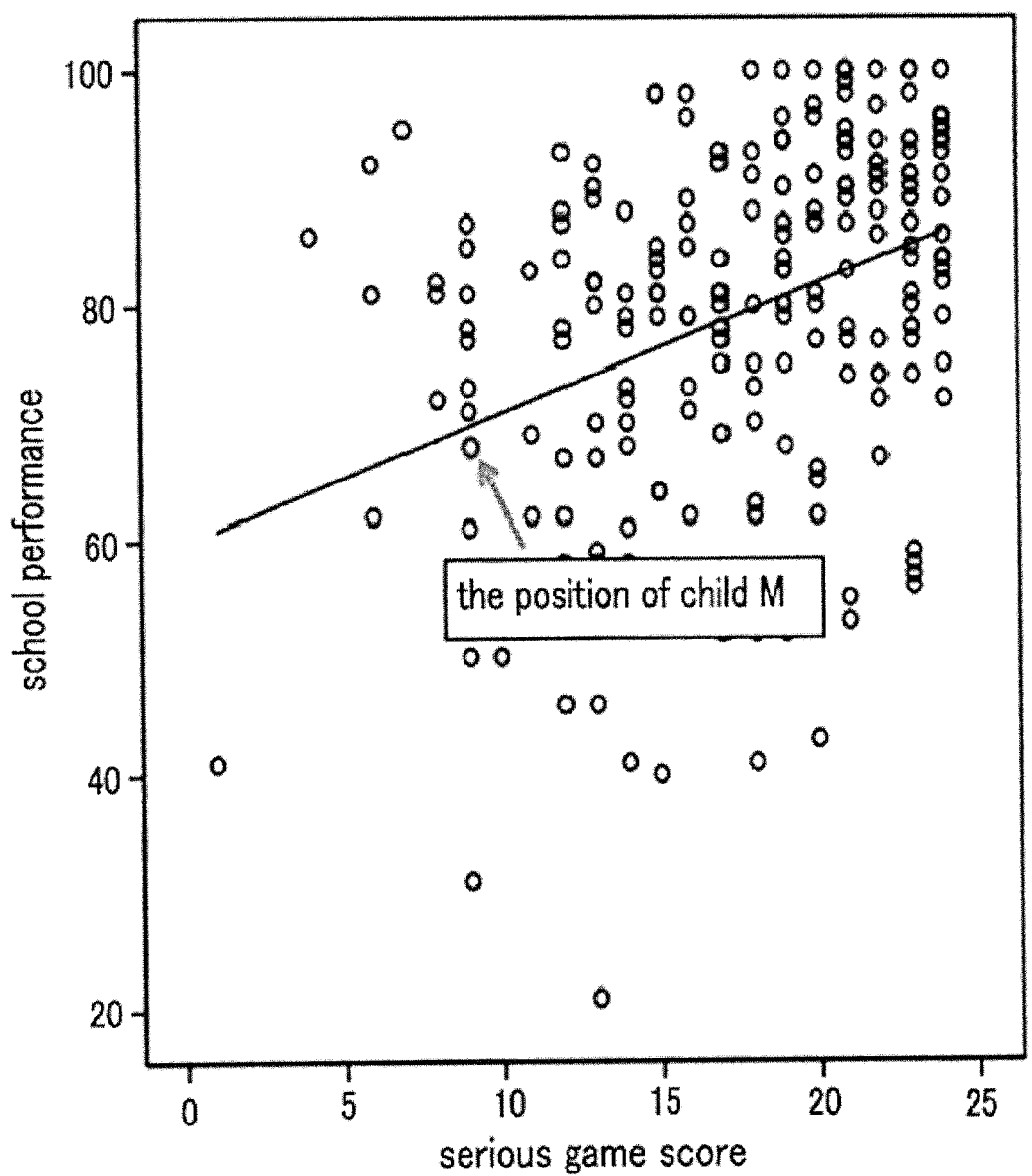

FIG. 9(*a*) provides a graph showing of a specific user (child M)'s achievement motivation, FIG. 9(*b*) provides a graph showing the correlation between the user's achievement motivation and school performance, and FIG. 9(*c*) provides a graph showing the correlation between the user's score in a game for attention and school performance.

The dysfunction diagnosis data generation unit 240 generates statistical dysfunction diagnosis data based on the game data, the representative value for each cognitive ability domain, and the intelligence pattern information. By way of example, the dysfunction diagnosis data generation unit 240 can extract the top 5% users and the bottom 5% users in each cognitive ability domain and analyze their various intelligence scores and questionnaire. FIG. 10(*a*) provides a graph showing the user (child G) belonging to the bottom 5% group and FIG. 10(*b*) provides a graph showing detailed indices of the user (child G) for various cognitive domains.

The result display unit 400 presents the user with the game data produced by the data processing unit 100 and various analysis data generated by the representative value calculation unit 210, the intelligence pattern generation unit 220, the learning ability analysis unit 230, and the dysfunction diagnosis data generation unit 240, through the result output interface, as depicted in FIGS. 11*a* to 11*d*.

As depicted in FIG. 11*a*, in some embodiments, the result display window provides polygonal diagram ① showing cognitive ability measurement results for each cognitive ability domain and their subcategories. The diagram ① shows that the more similar the polygon looks to a square, the more evenly are developed the user's cognitive abilities through all domains and their subcategories. Together with the diagram ①, the cognitive abilities pattern ② corresponding to the diagram ①, the total score of all cognitive abilities (hereinafter, referred to as "TQ") ③ as a comprehensive cognitive ability index, and the percentile rank ④ corresponding to the TQ may be further provided.

As depicted in FIG. 11*b*, the result display window may further provide a table ⑤ showing the TQ, corresponding percentile (position), and meaning (performance) for each cognitive ability domain, an image ⑥ showing related brain area for each cognitive ability domain, and a comment ⑦ of an expert about the table ⑤.

Figure 11C:
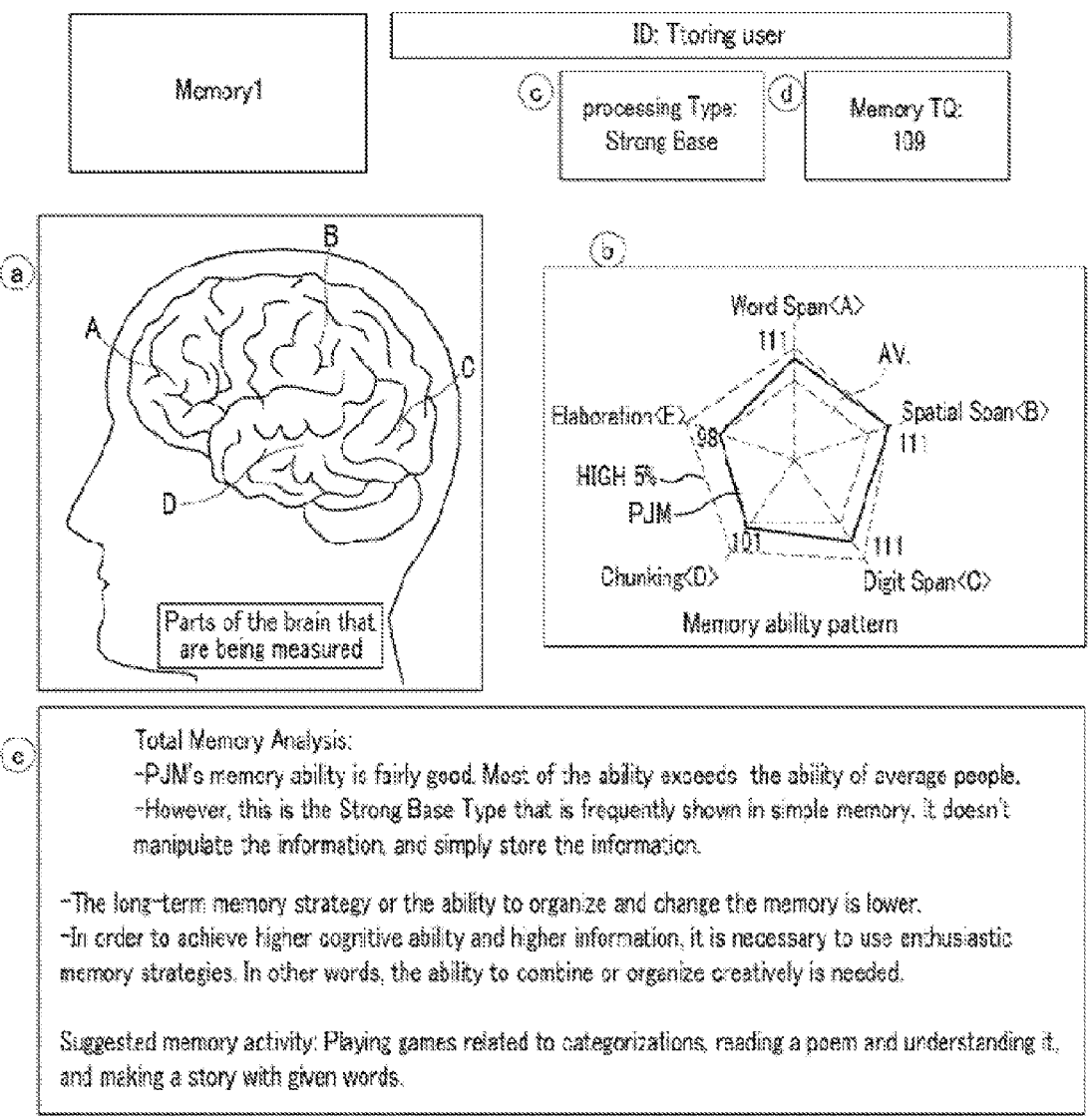

As depicted in FIG. 11*c*, for a specific cognitive ability domain (for example, "memory" as illustrated in FIG. 7*c*), the result display window may further provide an image ⓐ showing the related brain area, the polygonal diagram ⓑ showing the measurement results for each cognitive ability domain, the cognitive abilities pattern ⓒ corresponding to the diagram ⓑ, the TQⓓ, and the comment ⑦ of an expert about the polygonal diagram ⓑ.

Figure 11D:
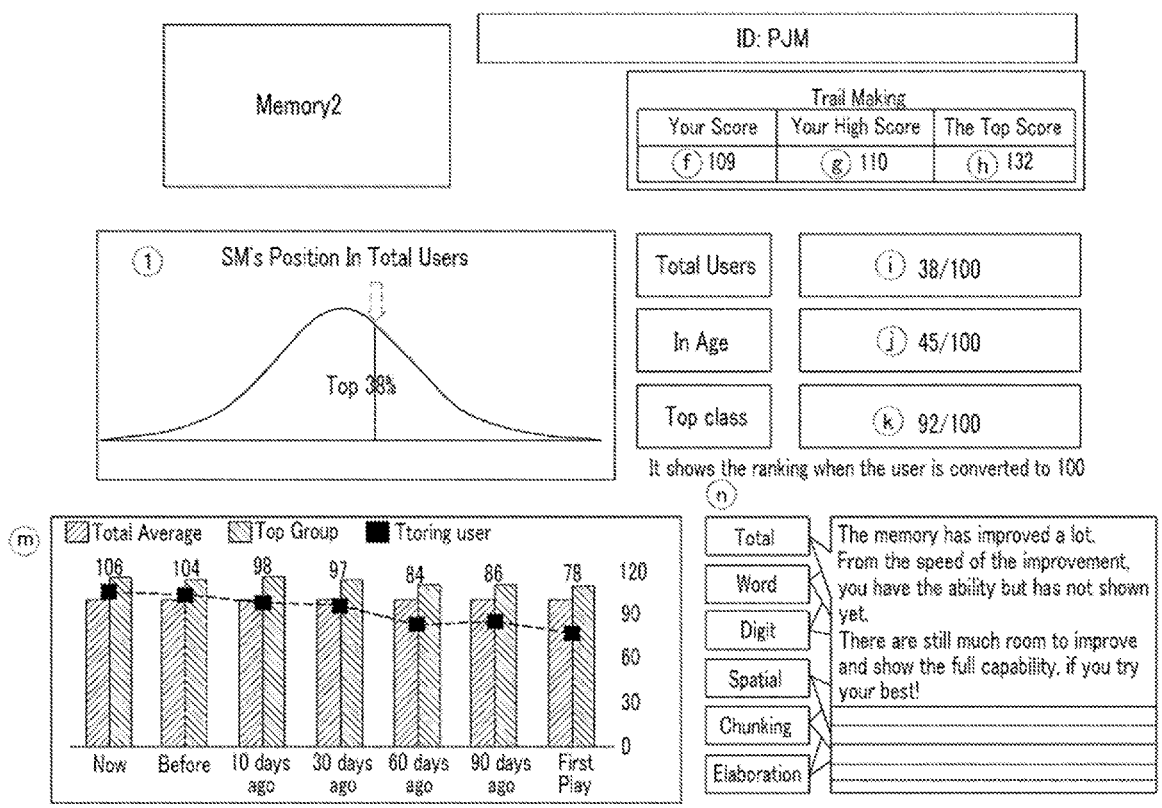

As depicted in FIG. 11*d*, the result display window may further provide the game score ⓕ of the user, the top score ⓖ of the user, and the top score ⓗ of total users. Furthermore, for the score ⓕ of the user, the result display window may provide the user's percentile rank ⓘ among the total users, percentile rank ⓙ among the same age group, and percentile rank ⓚ among the top class whose scorers are beyond at least the average score. Furthermore, the result display window may provide a graph ⓛ showing the user's percentile rank ⓙ among the total users, a histogram ⓜ showing changes in the user's scores for a certain period of time, and the comment ⓝ of an expert about the execution result of the user.

The result display unit 400 may provide the above-described analysis data to the user via various social network service (SNS) interfaces such as a blog, Twitter, Facebook, and the like.

Again, referring to FIG. 1, the game selection unit 500 selects one or more games to be executed from a plurality of games based on the game data produced by the data processing unit 100 or the analysis data produced by the analysis processing unit 200. By way of example, based on cognitive ability assessment data for a registered user, at least one game content is selected from a plurality of game contents and the level of each game is determined and then the selected games contents are recommended to the user. The user may select a specific game from the game recommendation list and execute the selected game.

The embodiment of the present invention can be embodied in a storage medium including instruction codes executable by a computer such as a program module executed by the computer. Besides, the data structure in accordance with the embodiment of the present invention can be stored in the storage medium executable by the computer. A computer readable medium can be any usable medium which can be accessed by the computer and includes all volatile/non-volatile and removable/non-removable media. Furthermore, the computer readable medium may include all computer storage and communication media. The computer storage medium includes all volatile/non-volatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes a certain information transmission medium.

The system and method of the present disclosure has been explained in relation to a specific embodiment, but its components or a part or all of its operation can be embodied by using a computer system having general-purpose hardware architecture.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A platform apparatus that processes the execution results of one or more serious games, the platform apparatus comprising:
a data processing unit that receives output packets produced from each serious game in execution for measuring and developing a user's cognitive abilities and that generates game data from the output packets;
an analysis processing unit that generates, based on the game data, analysis data for measuring the user's brain function; and
a result display unit that displays the analysis data to the user through an UI (user interface),
wherein the one or more serious game includes one or more of a serious game for memory, a serious game for psycho-motor, a serious game for attention, a serious game for executive function, and a serious game for emotion,
the output packets contain one or more of information of a user playing the serious game, information of a character used by the user during execution of the serious game, time information of the user for operating the input device, position information of a cursor the user controlling via the input device, information of a collision between the character and objects appearing in the serious game, a correct answer rate of the user's response to events in the game, and a reaction error rate of the user's response to the events, and
the game data contains one or more of a reaction time of the user to the events occurring during the execution of the serious game, a reaction error rate of the user's response to the events, and an accumulated distance of the cursor movement during the execution of the serious game.

2. The platform apparatus of claim 1,
wherein the data processing unit includes:
a filtering unit that filters the output packet and generates raw data;
a reaction time extraction unit that extracts the reaction time of the user from the raw data;
a reaction error rate extraction unit that extracts the reaction error rate of the user from the raw data; and
a cursor trace unit that extracts the accumulated distance of the cursor movement from the raw data.

3. The platform apparatus of claim 2,
wherein the data processing unit further includes:
a standardization unit that accumulates the information contained in the output packets for a certain time period to generate a normal distribution, and marks the input values out of a predetermined range in the normal distribution as errors.

4. The platform apparatus of claim 2,
wherein the data processing unit further includes:
a time-position information extraction unit that extracts, from the raw data, the reaction time of the user to two or more different objects appearing in the serious game and the difference of the positions where the input device was operated;
an error pattern generation unit that generates error pattern information from the raw data if the user reacted wrong; and
a questionnaire response management unit that handles the answers of the user to a questionnaire presented to the user.

5. The platform apparatus of claim 1,
wherein the analysis data contains one or more information including a representative value for each cognitive ability domain, generated based on the game data;
intelligence pattern information for each cognitive ability domain, generated based on the game data;

statistical learning ability comparison data, generated based on the game data and the representative value and intelligence pattern information for each cognitive ability domain; and statistical dysfunction diagnosis data, generated based on the game data and the representative value and intelligence pattern information for each cognitive ability domain.

6. The platform apparatus of claim 1, wherein the analysis processing unit includes:

a representative value calculation unit that calculates, based on the game data, a representative value for each cognitive ability domain;

an intelligence pattern generation unit that generates, based on the game data, intelligence pattern information for each cognitive ability domain;

a learning ability analysis unit that generates, based on the game data, the representative value and intelligence pattern information for each cognitive ability domain, statistical learning ability comparison data; and a dysfunction diagnosis data generation unit that generates, based on the game data, the representative value and intelligence pattern information for each cognitive ability domain, statistical dysfunction diagnosis data.

7. The platform apparatus of claim 1, wherein the result display unit provides the analysis data to the user via a social network service (SNS).

8. The platform apparatus of claim 1, further comprising:

a game selection unit that selects one or more games to be executed from a plurality of games, based on the game data produced by the data processing unit or the analysis data produced by the analysis processing unit.

* * * * *